US011975360B2

(12) United States Patent
Kwon et al.

(10) Patent No.: US 11,975,360 B2
(45) Date of Patent: May 7, 2024

(54) IMAGING DEVICES HAVING PIEZOELECTRIC TRANSCEIVERS WITH HARMONIC CHARACTERISTICS

(71) Applicant: Exo Imaging, Inc., Santa Clara, CA (US)

(72) Inventors: Haesung Kwon, Austin, TX (US); Brian Bircumshaw, Oakland, CA (US); Sandeep Akkaraju, Wellesley, MA (US)

(73) Assignee: EXO IMAGING, INC., Santa Clara, CA (US)

( * ) Notice: Subject to any disclaimer, the term of this patent is extended or adjusted under 35 U.S.C. 154(b) by 0 days.

(21) Appl. No.: 17/936,585

(22) Filed: Sep. 29, 2022

(65) Prior Publication Data
US 2023/0015764 A1    Jan. 19, 2023

Related U.S. Application Data

(62) Division of application No. 17/218,656, filed on Mar. 31, 2021.

(51) Int. Cl.
| B06B 1/06 | (2006.01) |
| G01H 11/08 | (2006.01) |
| G01N 29/24 | (2006.01) |
| B06B 1/02 | (2006.01) |
| H10N 30/20 | (2023.01) |

(52) U.S. Cl.
CPC ........... B06B 1/0622 (2013.01); G01H 11/08 (2013.01); G01N 29/2406 (2013.01); B06B 1/0292 (2013.01); H10N 30/2047 (2023.02)

(58) Field of Classification Search
None
See application file for complete search history.

(56) References Cited

U.S. PATENT DOCUMENTS

| 2,808,522 A | 10/1957 | Dranetz |
| 3,088,323 A | 5/1963 | Walter et al. |
| 4,156,800 A | 5/1979 | Sear et al. |
| 4,211,949 A | 7/1980 | Brisken et al. |
| 4,375,042 A | 2/1983 | Marcus |
| 4,445,063 A | 4/1984 | Smith |
| 4,517,842 A | 5/1985 | Twomey et al. |

(Continued)

FOREIGN PATENT DOCUMENTS

| CN | 1445872 A | 10/2003 |
| CN | 102577436 A | 7/2012 |

(Continued)

OTHER PUBLICATIONS

Covaci, Piezoelectric Energy Harvesting Solutions: A Review, Sensors (Year: 2020).*

(Continued)

*Primary Examiner* — Isam A Alsomiri
*Assistant Examiner* — Vikas Atmakuri
(74) *Attorney, Agent, or Firm* — Morgan, Lewis & Bockius LLP

(57) ABSTRACT

Described are micromachined ultrasonic transducers (MUTs) with convex or concave electrodes, which have enhanced pressure amplitude and frequency response behavior when driven at fundamental and harmonic frequencies, as well as methods of making the same.

21 Claims, 15 Drawing Sheets

(56) References Cited

U.S. PATENT DOCUMENTS

| | | | |
|---|---|---|---|
| 4,630,465 A | 12/1986 | Hatton | |
| 4,654,554 A | 3/1987 | Kishi | |
| 4,668,906 A | 5/1987 | Ekstrand | |
| 4,709,360 A | 11/1987 | Martin et al. | |
| 5,488,956 A | 2/1996 | Bartelt et al. | |
| 5,520,187 A | 5/1996 | Snyder | |
| 5,548,564 A | 8/1996 | Smith | |
| 5,722,411 A | 3/1998 | Suzuki | |
| 5,825,117 A | 10/1998 | Ossmann et al. | |
| 5,945,770 A | 8/1999 | Hanafy | |
| 6,051,895 A | 4/2000 | Mercier | |
| 6,108,121 A | 8/2000 | Mansell et al. | |
| 7,382,635 B2 | 6/2008 | Noda | |
| 7,532,093 B1 | 5/2009 | Pulskamp et al. | |
| 8,004,158 B2 | 8/2011 | Hielscher | |
| 8,626,295 B2 | 1/2014 | Doron et al. | |
| 9,067,779 B1 | 6/2015 | Rothberg et al. | |
| 9,393,597 B2* | 7/2016 | Clark | B06B 1/0637 |
| 9,479,875 B2 | 10/2016 | Hall et al. | |
| 10,106,397 B1 | 10/2018 | Kim et al. | |
| 10,648,852 B2 | 5/2020 | Akkaraju et al. | |
| 10,656,007 B2 | 5/2020 | Akkaraju et al. | |
| 10,969,270 B2 | 4/2021 | Akkaraju et al. | |
| 11,039,814 B2 | 6/2021 | Akkaraju et al. | |
| 2002/0109436 A1 | 8/2002 | Peng et al. | |
| 2004/0039246 A1 | 2/2004 | Gellman | |
| 2004/0085858 A1 | 5/2004 | Khuri-Yakub et al. | |
| 2005/0134574 A1 | 6/2005 | Hill | |
| 2005/0146247 A1* | 7/2005 | Fisher | G01N 29/2406 |
| | | | 310/334 |
| 2005/0148132 A1 | 7/2005 | Wodnicki | |
| 2005/0200242 A1 | 9/2005 | Degertekin | |
| 2006/0113866 A1 | 6/2006 | Ganor | |
| 2007/0103697 A1 | 5/2007 | Degertekin | |
| 2007/0197922 A1 | 8/2007 | Bradley et al. | |
| 2007/0205698 A1 | 9/2007 | Chaggares et al. | |
| 2008/0048211 A1 | 2/2008 | Khuri-Yakub et al. | |
| 2009/0001853 A1 | 1/2009 | Adachi et al. | |
| 2009/0250729 A1 | 10/2009 | Lemmerhirt et al. | |
| 2010/0168583 A1 | 7/2010 | Dausch et al. | |
| 2010/0225204 A1* | 9/2010 | Hamann | H10N 30/508 |
| | | | 29/25.35 |
| 2010/0256501 A1 | 10/2010 | Degertekin | |
| 2010/0301227 A1 | 12/2010 | Muntean | |
| 2010/0327695 A1 | 12/2010 | Goel et al. | |
| 2011/0051461 A1 | 3/2011 | Buchwald et al. | |
| 2012/0091543 A1 | 4/2012 | Torashima et al. | |
| 2012/0103096 A1 | 5/2012 | Kandori | |
| 2012/0127136 A1 | 5/2012 | Schneider et al. | |
| 2012/0187508 A1 | 7/2012 | Adler et al. | |
| 2012/0206014 A1 | 8/2012 | Bibl et al. | |
| 2012/0250454 A1 | 10/2012 | Rohling et al. | |
| 2012/0289897 A1 | 11/2012 | Friend et al. | |
| 2012/0319174 A1 | 12/2012 | Wang | |
| 2013/0039147 A1 | 2/2013 | Witte et al. | |
| 2013/0234559 A1* | 9/2013 | Ermolov | B82Y 30/00 |
| | | | 310/321 |
| 2013/0293065 A1 | 11/2013 | Hajati et al. | |
| 2013/0294201 A1 | 11/2013 | Hajati | |
| 2013/0331705 A1 | 12/2013 | Fraser | |
| 2014/0019072 A1 | 1/2014 | Alles | |
| 2014/0117812 A1 | 5/2014 | Hajati | |
| 2014/0145561 A1 | 5/2014 | Jin et al. | |
| 2014/0219063 A1 | 8/2014 | Hajati et al. | |
| 2014/0220723 A1 | 8/2014 | Liu et al. | |
| 2014/0225476 A1 | 8/2014 | Degertekin et al. | |
| 2014/0328504 A1 | 11/2014 | Stephanou et al. | |
| 2015/0097468 A1 | 4/2015 | Hajati et al. | |
| 2015/0250452 A1 | 9/2015 | Jin et al. | |
| 2015/0265245 A1 | 9/2015 | Von Ramm et al. | |
| 2016/0027991 A1 | 1/2016 | Suzuki | |
| 2016/0045935 A1 | 2/2016 | Yoon et al. | |
| 2016/0105748 A1 | 4/2016 | Pal et al. | |
| 2016/0107194 A1* | 4/2016 | Panchawagh | G10K 11/34 |
| | | | 310/317 |
| 2016/0136686 A1 | 5/2016 | Brock-Fisher | |
| 2016/0136687 A1 | 5/2016 | Lewis, Jr. et al. | |
| 2016/0262725 A1 | 9/2016 | Boser et al. | |
| 2017/0021391 A1 | 1/2017 | Guedes et al. | |
| 2017/0170383 A1* | 6/2017 | Sammoura | G10K 11/32 |
| 2017/0209121 A1 | 7/2017 | Davis, Sr. et al. | |
| 2017/0232474 A1 | 8/2017 | Oralkan et al. | |
| 2017/0309808 A1 | 10/2017 | Hada et al. | |
| 2017/0319180 A1 | 11/2017 | Henneken et al. | |
| 2017/0322290 A1 | 11/2017 | Ng et al. | |
| 2017/0368574 A1* | 12/2017 | Sammoura | B06B 1/0622 |
| 2018/0153510 A1 | 6/2018 | Haque et al. | |
| 2019/0176193 A1 | 6/2019 | Shulepov et al. | |
| 2019/0257943 A1* | 8/2019 | Beers | B06B 1/02 |
| 2019/0316957 A1* | 10/2019 | Akkaraju | G01S 15/02 |
| 2019/0316958 A1* | 10/2019 | Akkaraju | G01N 29/0654 |
| 2020/0205776 A1 | 7/2020 | Dekker et al. | |
| 2020/0249079 A1 | 8/2020 | Akkaraju et al. | |
| 2020/0266798 A1 | 8/2020 | Shelton et al. | |
| 2021/0069748 A1 | 3/2021 | Bircumshaw et al. | |
| 2021/0078042 A1 | 3/2021 | Bircumshaw et al. | |
| 2021/0151661 A1 | 5/2021 | Kwon et al. | |
| 2021/0172788 A1 | 6/2021 | Akkaraju et al. | |
| 2021/0236090 A1 | 8/2021 | Akkaraju et al. | |
| 2021/0278927 A1* | 9/2021 | Jennings | H10N 30/87 |
| 2021/0364348 A1 | 11/2021 | Akkaraju et al. | |
| 2022/0314275 A1 | 10/2022 | Kwon | |

FOREIGN PATENT DOCUMENTS

| | | |
|---|---|---|
| CN | 104271266 A | 1/2015 |
| CN | 104984890 A | 10/2015 |
| CN | 105310718 A | 2/2016 |
| CN | 106500824 A | 3/2017 |
| CN | 106999163 A | 8/2017 |
| EP | 3453056 A1 | 3/2019 |
| JP | S6276392 A | 4/1987 |
| JP | H06350155 A | 12/1994 |
| JP | 2002026681 A | 1/2002 |
| JP | 2007510324 A | 4/2007 |
| JP | 2009165212 A | 7/2009 |
| JP | 2013123150 A | 6/2013 |
| JP | 2014000122 A | 1/2014 |
| JP | 2014127921 A | 7/2014 |
| JP | 2016503312 A | 2/2016 |
| JP | 2018046512 A | 3/2018 |
| WO | WO-2006123300 A2 | 11/2006 |
| WO | WO-2007099696 A1 | 9/2007 |
| WO | WO-2009088307 A1 | 7/2009 |
| WO | WO-2011026187 A1 | 3/2011 |
| WO | WO-2011033887 A1 | 3/2011 |
| WO | WO-2012117996 A1 | 9/2012 |
| WO | WO-2013043906 A1 | 3/2013 |
| WO | WO-2013158348 A1 | 10/2013 |
| WO | WO-2015131083 A1 | 9/2015 |
| WO | WO-2017025438 A1 | 2/2017 |
| WO | WO-2017132517 A1 | 8/2017 |
| WO | WO-2017182344 A1 | 10/2017 |
| WO | WO-2017216139 A1 | 12/2017 |
| WO | WO-2018102223 A1 | 6/2018 |
| WO | WO-2019164721 A1 | 8/2019 |
| WO | WO-2019199397 A1 | 10/2019 |
| WO | WO-2019199398 A1 | 10/2019 |
| WO | WO-2019226547 A1 | 11/2019 |
| WO | WO-2020028580 A1 | 2/2020 |
| WO | WO-2021050853 A1 | 3/2021 |

OTHER PUBLICATIONS

Aabid, A Systematic Review of Piezoelectric Materials and Energy Harvesters for Industrial Applications, Sensors (Year: 2021).

Xiang, Static analysis for multi-layered piezoelectric cantilevers, International Journal of Solids and Structures (Year: 2007).

U.S. Appl. No. 17/180,308 Office Action dated Dec. 10, 2021.

APC International, Ceramic manufacturing series—poling PZT ceramics. https ://www .a merican piezo. com/blog/ceramic-manufacturing-series-po ling-pzt-ceramics/ [1-3] (2016).

(56) References Cited

OTHER PUBLICATIONS

Assef et al., A reconfigurable arbitrary waveform generator using PWM modulation for ultrasound research. BioMedical Engineering Online 12:24 [1-13] (2013).
Choudhry et al., Comparison of tissue harmonic imaging with conventional US in abdominal disease. RadioGraphics: Imaging and Therapeutic Technology 20:1127-1135 (2000).
Dahl, Ultrasound beamforming and image formation. http://people.duke.edu/-jjd/RSNA_USbeamforming.pdf [Slide presentation] (c. 2005).
Dausch et al., Theory and operation of 2-D array piezoelectric micromachined ultrasound transducers. IEEE Transactions on Ultrasonics, Ferroelectrics, and Frequency Control 55(11):2484-2492 (2008).
Doerry, Generating nonlinear FM chirp waveforms for radar. Sandia Report, SAND2006-5856: 1-34 (2006).
Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).
Goldman, Apple's Lightning connector and you: what you should know. CNET Sep. 19, 2012: https://www.cnet.com/news/apples-lightning-connector-and-you-what-you-should-know/ (2012).
Guedes et al., Aluminum nitride pMUT based on a flexurally-suspended membrane. IEEE 16th International Solid-State Sensors, Actuators and Microsystems Conference: 12169346 (2011).
Hajati et al., Three-dimensional micro electromechanical system piezoelectric ultrasound transducer. Appl. Phys. Lett. 101:253101 (2012).
Harput, Use of chirps in medical ultrasound imaging. Ultrasound Group, School of Electronic and Electrical Engineering, University of Leeds, PHD Thesis, Dec. 2012.
Karki, Signal conditioning piezoelectric sensors. Texas Instruments Application report, SLA033A:1-5 (2000).
Khuri-Yakub et al., Capacitive micro machined ultrasonic transducers for medical imaging and therapy. Journal of Micromech Microeng. 21 (5):054004-054014 (2011).
Lach et al., Piezoelectric materials for ultrasonic probes. http://www.ndt.neUarticle/platte2/platte2.htm NDTnet 1 (9):1-9 (1996).
Lee et al., Wafer-to-wafer alignment for three-dimensional integration: a review. Journal of MicroElectroMechanical Systems 20(4):885-898 (2011).
Lu et al., High frequency piezoelectric micromachined ultrasonic transducer array for intravascular ultrasound imaging. Proceedings of the IEEE International Conference on Micro Electro Mechanical Systems (MEMS):06765748 (2014).
Martin, Introduction to B-mode imaging. Cambridge University Press; Diagnostic Ultrasound: Physics and equipment, 2nd Edition. Chapter 1 :1-10 (2010).
Mina, High frequency transducers from PZT films. Materials Science and Engineering Thesis; Pennsylvania State University: 1-199 (2007).
Moazzami et al., Electrical characteristics of ferroelectric PZT thin films for DRAM applications. IEEE Transaction on Electron Devices 39(9):2044-2049 (1992).
Orenstein Scanning in pain—sonographers seek relief from job-related hazard. Radiology Today 10(8):24 (2009).
Ovland, Coherent plane-wave compounding in medical ultrasound imaging. NTNU-Trondheim, Norwegian University of Science and Technology, Master of Science Thesis, 1-62 (Jun. 2012).
PCT/US2017/063163 International Search Report and Written Opinion dated Feb. 15, 2018.
PCT/US2019/021501 International Search Report and Written Opinion dated Jul. 12, 2019.
PCT/US2019/021515 International Search Report and Written Opinion dated May 31, 2019.
PCT/US2019/033119 International Search Report and Written Opinion dated Aug. 9, 2019.
PCT/US2019/044528 International Search Report and Written Opinion dated Oct. 16, 2019.
PCT/US2020/050374 International Search Report and Written Opinion dated Feb. 2, 2021.
PCT/US2020/050374 Invitation to Pay Additional Fees dated Nov. 13, 2020.
PCT/US2021/024667 International Search Report and Written Opinion dated Jul. 8, 2021.
PCT/US2021/025109 International Search Report and Written Opinion dated Jul. 7, 2021.
Pye et al., Adaptive time gain compensation for ultrasonic imaging. Ultrasound in Medicine and Biology 18(2):205-212 [abstract] (1992).
Rodriguez et al., Low cost matching network for ultrasonic transducers. Physics Procedia 3:1025-1031 (2010).
Smyth, Design and modeling of a PZT thin film based piezoelectric micromachined ultrasonic transducer (PMUT). MSME Thesis, MIT:1-156 (2012).
Spectral doppler. http://www.echocardiographer.org/Echo%20Physics/spectral%20doppler.html (2017).
Szabo. Diagnostic ultrasound imaging: inside out. Elsevier Academic Press, ISBN: 0-12-680145-2 (572 pgs) (2014).
Trots et al., Synthetic aperture method in ultrasound imaging. InTech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).
U.S. Appl. No. 15/820,319 Office Action dated May 14, 2020.
U.S. Appl. No. 15/951,118 Office Action dated Sep. 20, 2019.
U.S. Appl. No. 15/951,121 Office Action dated May 6, 2019.
U.S. Appl. No. 15/951,121 Office Action dated Nov. 19, 2019.
U.S. Appl. No. 16/837,800 Office Action dated Sep. 8, 2020.
U.S. Appl. No. 16/837,800 Office Action dated May 7, 2021.
Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015): 15260900. Xi'an, China, Apr. 7-11, 2015.
Wang et al., Zero-bending piezoelectric micromachined ultrasonic transducer (pMUT) with enhanced transmitting performance. Journal of Microelectromechanical Systems 24(6):2083-2091 (2015).
Zhang et al. Double-SOI wafer-bonded CMUTs with improved electrical safety and minimal roughness of dielectric and electrode surfaces. Journal of microelectromechanical systems 21(3):668-680 (2012).
Co-pending U.S. Appl. No. 17/215,776, inventors Bircumshaw; Brian et al., filed Mar. 29, 2021.
Co-pending U.S. Appl. No. 17/364,381, inventors Mantravadi; Naresh et al., filed Jun. 30, 2021.
Co-pending U.S. Appl. No. 17/364,397, inventors Kwon; Haesung et al., filed Jun. 30, 2021.
Hill et al. The Role Radius of Curvature Plays in Thiolated Oligonucleotide Loading on Gold Nanopartictes. ACS Nano 3(2):418-424 (2009) Retrieved on Sep. 2, 2021 from https://www.ncbi.nlm.nih.gov/pmc/articles/PMC3241534.
PCT/US2021/039977 International Search Report and Written Opinion dated Oct. 6, 2021.
PCT/US2021/039994 International Search Report and Written Opinion dated Nov. 5, 2021.

* cited by examiner

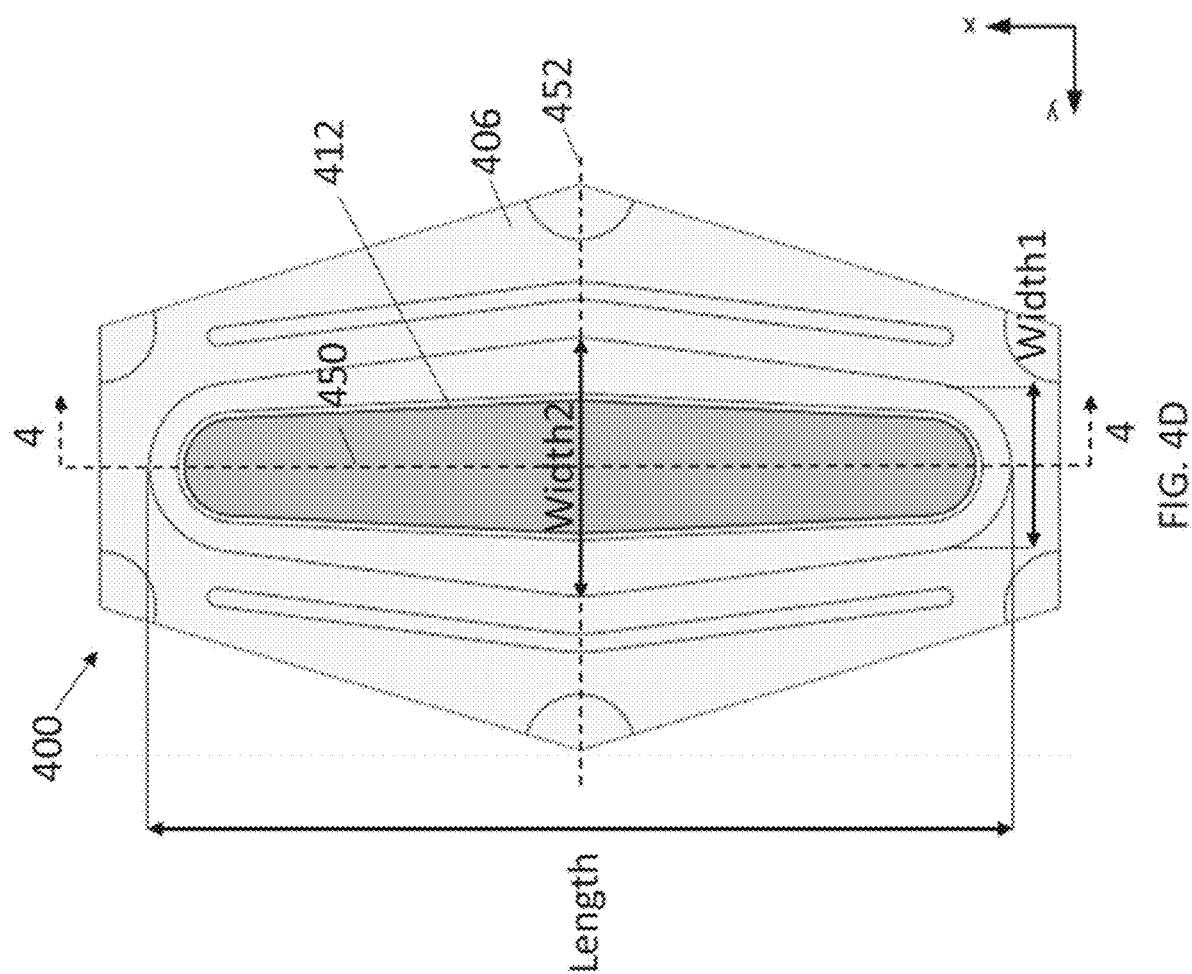

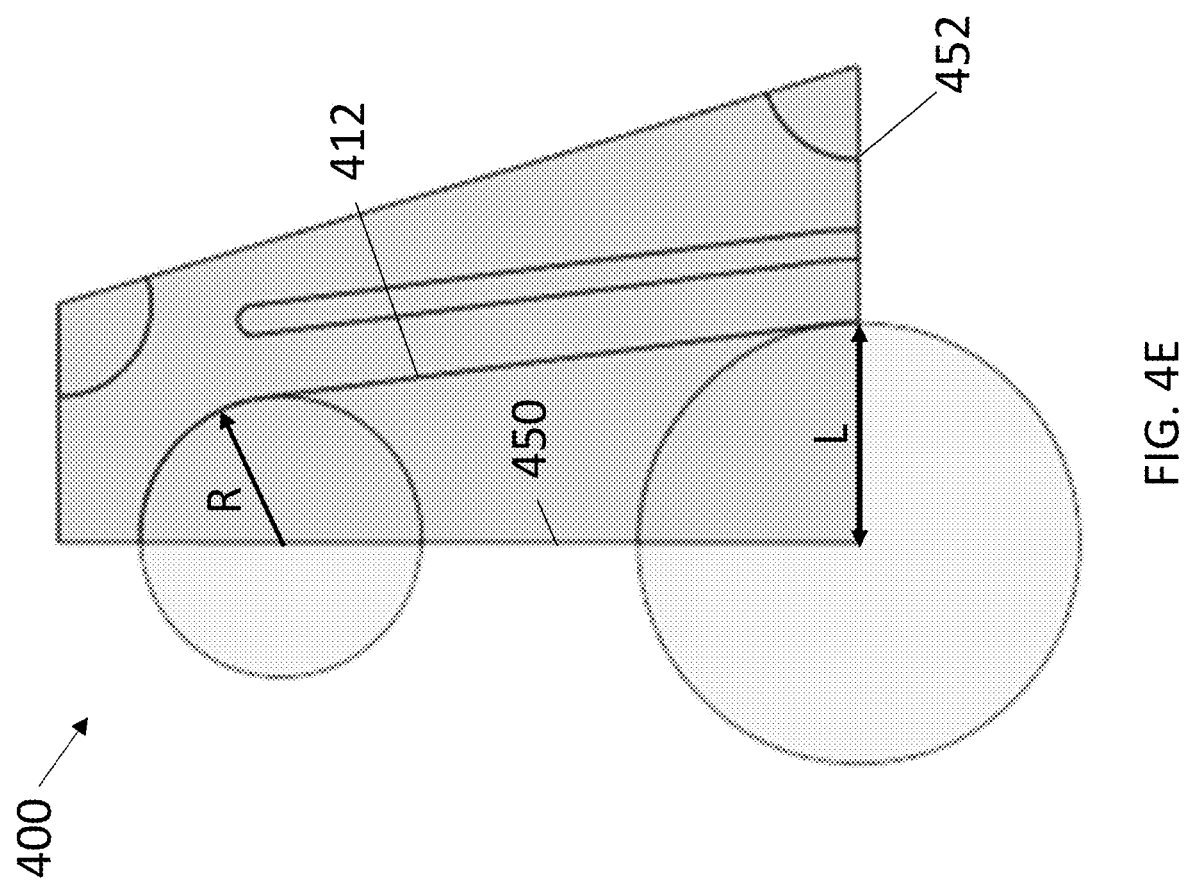

IMAGING DEVICES HAVING PIEZOELECTRIC TRANSCEIVERS WITH HARMONIC CHARACTERISTICS

CROSS-REFERENCE

This application is a divisional of U.S. patent application Ser. No. 17/218,656, filed Mar. 31, 2021, which is entirely incorporated herein by reference.

BACKGROUND

Technical Field

The present invention relates to imaging devices and, more particularly, to imaging devices having micromachined ultrasound transducers (MUTs) that exhibit enhanced pressure amplitude and frequency response behavior when driven at fundamental and harmonic frequencies.

Background

A non-intrusive imaging system for imaging internal organs of a human body and displaying images of the internal organs transmits signals into the human body and receives signals reflected from the organs. Typically, transducers, such as capacitive transducers (cMUTs) or piezoelectric transducers (pMUTs), that are used in an imaging system are referred to as transceivers and some of the transceivers are based on photo-acoustic or ultrasonic effects.

In general, a MUT includes two or more electrodes and the topology of the electrodes affects both electrical and acoustic performances of the MUT. For instance, the amplitude of acoustic pressure generated by a pMUT increases as the size of the electrodes increase, to thereby improve the acoustic performance of the pMUT. However, as the size of the electrodes increase, the capacitance also increases to degrade the electrical performance of the pMUT. In another example, the amplitude of acoustic pressure at a vibrational resonance frequency of the pMUT is affected by the shape of the electrodes. As such, there is a need for methods for designing electrodes to enhance both acoustical and electrical performances of the transducers.

SUMMARY

In embodiments, a micromachined ultrasonic transducer (MUT) includes a top electrode. The shape of the top electrode is defined by a major and minor axis, where the major and minor axis intersect at an origin point. Both distal ends of the top electrode, i.e., the ends of the top electrode farthest from the origin in the direction of the major axis, are defined by radius of curvature, R. The characteristic width of the top electrode, L, is measured from the origin, in the direction of the minor axis (i.e., normal to the major axis), to the top electrode outer edge or perimeter. When the ratio of the radius of curvature over the characteristic width, R/L, is more than one, the top electrode is wider at its ends as compared to its width at the middle, and the electrode has a generally concave geometry. When the ratio of the radius of curvature over the characteristic width, R/L, is less than one, the top electrode is narrower at its ends as compared to its width at the middle, and the electrode has a generally convex geometry. As set forth in greater detail herein, whether configured with either concave or convex geometry, electrodes with certain R/L, values or within certain value ranges exhibit desirable pressure amplitude and frequency response behavior when driven at fundamental and harmonic frequencies, relative to prior electrode shape designs. The areal density distribution of the concave or convex electrode along an axis has a plurality of local maxima, wherein locations of the plurality of local maxima coincide with locations where a plurality of anti-nodal points at a vibrational resonance frequency are located.

In embodiments, a micromachined ultrasonic transducer (MUT) includes a symmetric convex top electrode. The areal density distribution of the symmetric convex electrode along an axis has a plurality of local maxima, wherein locations of the plurality of local maxima coincide with locations where a plurality of anti-nodal points at a vibrational resonance frequency are located.

In embodiments, a transducer array includes a plurality of micromachined ultrasonic transducers (MUTs). Each of the plurality of MUTs includes a symmetric convex top electrode.

In embodiments, an imaging device includes a transducer array that has a plurality of micromachined ultrasonic transducers (MUTs). Each of the plurality of MUTs includes a symmetric convex top electrode. The areal density distribution of the symmetric convex electrode along an axis has a plurality of local maxima and wherein locations of the plurality of local maxima coincide with locations where a plurality of anti-nodal points at a vibrational resonance frequency are located.

In embodiments, a micromachined ultrasonic transducer (MUT) includes a symmetric concave top electrode. The areal density distribution of the symmetric concave electrode along an axis has a plurality of local maxima, wherein locations of the plurality of local maxima coincide with locations where a plurality of anti-nodal points at a vibrational resonance frequency are located.

In embodiments, a transducer array includes a plurality of micromachined ultrasonic transducers (MUTs). Each of the plurality of MUTs includes a symmetric concave top electrode.

In embodiments, an imaging device includes a transducer array that has a plurality of micromachined ultrasonic transducers (MUTs). Each of the plurality of MUTs includes a symmetric concave top electrode. The areal density distribution of the symmetric concave electrode along an axis has a plurality of local maxima and wherein locations of the plurality of local maxima coincide with locations where a plurality of anti-nodal points at a vibrational resonance frequency are located.

In a first aspect, a micromachined ultrasonic transducer (MUT) is provided. The MUT comprises a first electrode having first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its widest point along the first axis is at least two times L such that the first electrode has a convex shape and R/L, is less than 1.

In embodiments, the MUT is a capacitive micromachined ultrasound transducer (cMUT).

In embodiments, the MUT is a piezoelectric micromachined ultrasound transducer (pMUT).

In embodiments, the first axis extends along a direction where the first electrode has a longest dimension.

In embodiments, the second axis extends along a direction where the first electrode has a shortest dimension.

In embodiments, the MUT further comprises a substrate; a membrane suspending from the substrate; a second electrode disposed on the membrane; and a piezoelectric layer disposed on one or more of the first electrode or the second electrode. In some embodiments, the piezoelectric layer comprises a first piezoelectric layer disposed on the second electrode. In some embodiments, the MUT further comprises a third electrode disposed on the first piezoelectric layer; and a second piezoelectric layer disposed on the third electrode, wherein the first electrode is disposed on the second piezoelectric layer. In embodiments, the piezoelectric layer is formed of at least one of PZT, KNN, PZT-N, PMN-Pt, AlN, Sc-AlN, ZnO, PVDF, and $LiNiO_3$.

In another aspect, an imaging device is provided. The imaging device comprises a transducer array including a plurality of micromachined ultrasonic transducers (MUTs), each of the plurality of MUTs comprising a convex electrode.

In another aspect, an MUT is provided. The MUT comprises a first electrode having first and second ends along a first axis. One or more of the first end or second end is defined by a radius of curvature R. A second axis passes through a midpoint of the first axis, wherein the second axis is normal to the first axis. A half-width of the first electrode is defined by a length L measured from the midpoint, in the direction of the second axis, to an outer perimeter of the first electrode. A total width of the first electrode at its narrowest point along the first axis is less than 2 L such that the first electrode has a concave shape and R/L, is greater than 1.

In embodiments, the MUT is a capacitive micromachined ultrasound transducer (cMUT).

In embodiments, the MUT is a piezoelectric micromachined ultrasound transducer (pMUT).

In embodiments, the first axis extends along a direction where the first electrode has a longest dimension.

In embodiments, the second axis extends along a direction where the first electrode has a shortest dimension.

In embodiments, the MUT further comprises a substrate; a membrane suspending from the substrate; a second electrode disposed on the membrane; and a piezoelectric layer disposed on one or more of the first electrode or the second electrode. In some embodiments, the piezoelectric layer comprises a first piezoelectric layer disposed on the second electrode. In some embodiments, the MUT further comprises a third electrode disposed on the first piezoelectric layer; and a second piezoelectric layer disposed on the third electrode, wherein the first electrode is disposed on the second piezoelectric layer. In embodiments, the piezoelectric layer is formed of at least one of PZT, KNN, PZT-N, PMN-Pt, AlN, Sc-AlN, ZnO, PVDF, and $LiNiO_3$.

In another aspect, an imaging device is provided. The imaging device comprises a transducer array including a plurality of micromachined ultrasonic transducers (MUTs), each of the plurality of MUTs comprising a concave electrode.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

Figure (or "FIG.") 1 shows an imaging system according to embodiments of the present disclosure.

FIG. 4D shows a top view of a convex MUT according to embodiments of the present disclosure.

FIG. 4E shows an alternative top view of a convex MUT according to embodiments of the present disclosure.

DETAILED DESCRIPTION

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, or a device.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Figure 1:
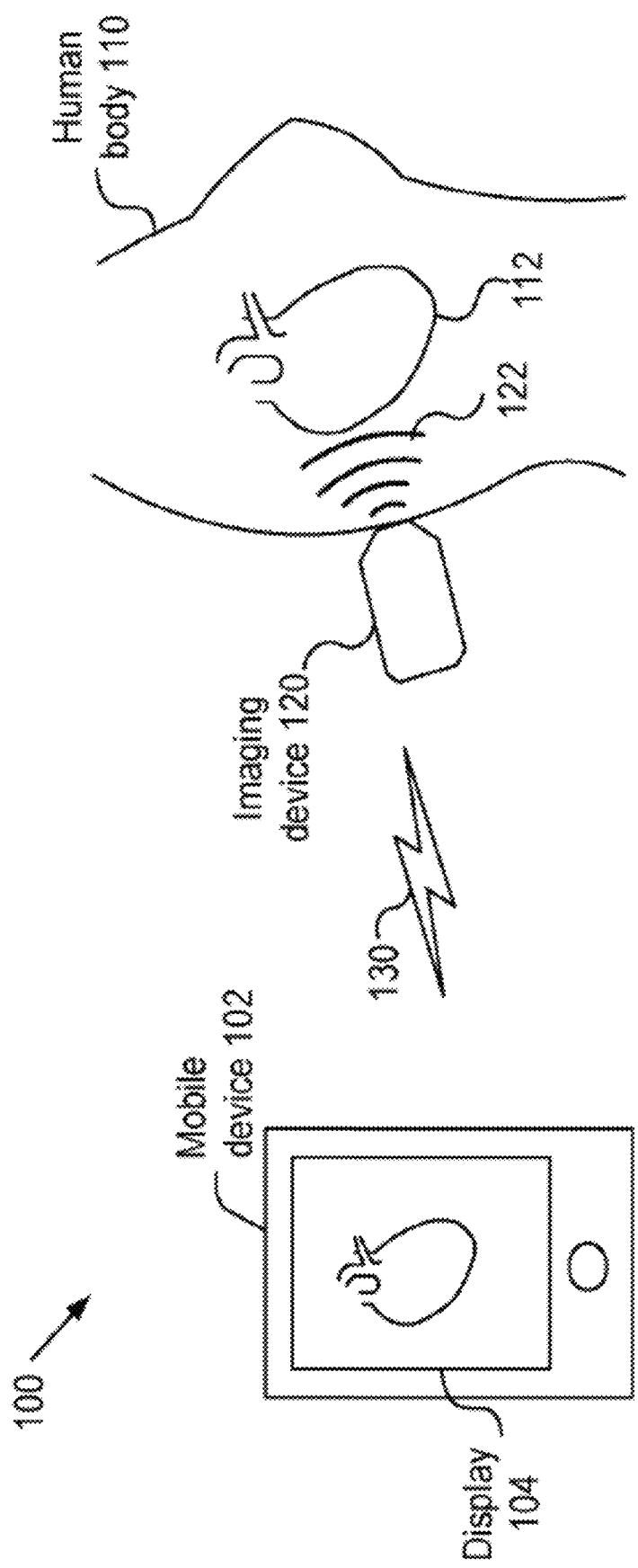

FIG. 1 shows a schematic diagram of an imaging system 100 according to embodiments of the present disclosure. As depicted, the system 100 may include: an imager 120 that generates and transmits pressure waves 122 toward an internal organ 112, such as heart, in a transmit mode/process and receives pressure waves reflected from the internal organ; and a device 102 that sends and receives signals to the imager through a communication channel 130. In embodiments, the internal organ 112 may reflect a portion of the pressure waves 122 toward the imager 120, and the imager 120 may capture the reflected pressure waves and generate electrical signals in a receive mode/process. The imager 120 may communicate electrical signals to the device 102 and the device 102 may display images of the organ or target on a display/screen 104 using the electrical signals.

In embodiments, the imager 120 may be used to get an image of internal organs of an animal, too. The imager 120 may also be used to determine direction and velocity of blood flow in arteries and veins as in Doppler mode imaging and also measure tissue stiffness. In embodiments, the pressure wave 122 may be acoustic waves that can travel through the human/animal body and be reflected by the internal organs, tissue or arteries and veins.

In embodiments, the imager 120 may be a portable device and communicate signals through the communication channel 130, either wirelessly (using a protocol, such as 802.11 protocol) or via a cable (such as USB2, USB 3, USB 3.1, USB-C, and USB thunderbolt), with the device 102. In embodiments, the device 102 may be a mobile device, such as cell phone or iPad, or a stationary computing device that can display images to a user.

In embodiments, more than one imager may be used to develop an image of the target organ. For instance, the first imager may send the pressure waves toward the target organ while the second imager may receive the pressure waves reflected from the target organ and develop electrical charges in response to the received waves.

Figure 2:
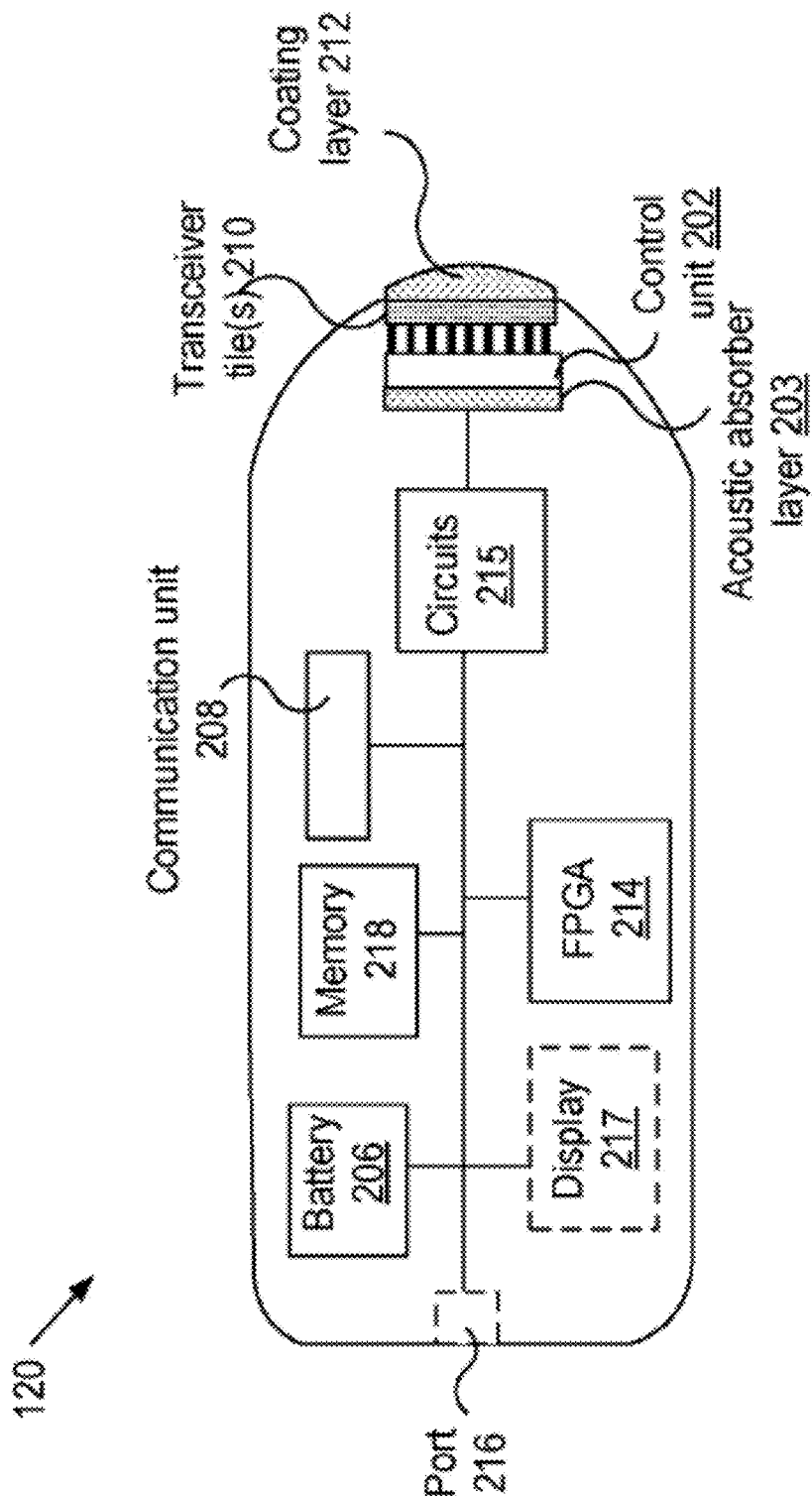
FIG. 2 shows a schematic diagram of an imager according to embodiments of the present disclosure.

FIG. 2 shows a schematic diagram of the imager 120 according to embodiments of the present disclosure. In embodiments, the imager 120 may be an ultrasonic imager. As depicted in FIG. 2, the imager 120 may include: a transceiver tile(s) 210 for transmitting and receiving pressure waves; a coating layer(s) 212 that operate as a lens for setting the propagation direction of and/or focusing the pressure waves and also functions as an acoustic impedance interface between the transceiver tile and the human body 110; a control unit 202, such as ASIC chip (or, shortly ASIC), for controlling the transceiver tile(s) 210 and coupled to the transducer tile 210 by bumps; Field Programmable Gate Arrays (FPGAs) 214 for controlling the components of the imager 120; a circuit(s) 215, such as Analogue Front End (AFE), for processing/conditioning signals; an acoustic absorber layer 203 for absorbing waves that are generated by the transducer tiles 210 and propagate toward the circuit 215; a communication unit 208 for communicating data with an external device, such as the device 102, through one or more ports 216; a memory 218 for storing data; a battery 206 for providing electrical power to the components of the imager; and optionally a display 217 for displaying images of the target organs.

In embodiments, the device 102 may have a display/screen. In such a case, the display may not be included in the imager 120. In embodiments, the imager 120 may receive electrical power from the device 102 through one of the ports 216. In such a case, the imager 120 may not include the battery 206. It is noted that one or more of the components of the imager 120 may be combined into one integral electrical element. Likewise, each component of the imager 120 may be implemented in one or more electrical elements.

In embodiments, the user may apply gel on the skin of the human body 110 before the body 110 makes a direct contact with the coating layer 212 so that the impedance matching at the interface between the coating layer 212 and the human body 110 may be improved, i.e., the loss of the pressure wave 122 at the interface is reduced and the loss of the reflected wave travelling toward the imager 120 is also reduced at the interface. In embodiments, the transceiver tiles 210 may be mounted on a substrate and may be attached to an acoustic absorber layer. This layer absorbs any ultrasonic signals that are emitted in the reverse direction, which may otherwise be reflected and interfere with the quality of the image.

As discussed below, the coating layer 212 may be only a flat matching layer just to maximize transmission of acoustic signals from the transducer to the body and vice versa. Beam focus is not required in this case, because it can be electronically implemented in control unit 202. The imager 120 may use the reflected signal to create an image of the organ 112 and results may be displayed on a screen in a variety of format, such as graphs, plots, and statistics shown with or without the images of the organ 112.

In embodiments, the control unit 202, such as ASIC, may be assembled as one unit together with the transceiver tiles. In other embodiments, the control unit 202 may be located outside the imager 120 and electrically coupled to the transceiver tile 210 via a cable. In embodiments, the imager 120 may include a housing that encloses the components 202-215 and a heat dissipation mechanism for dissipating heat energy generated by the components.

Figure 3A:
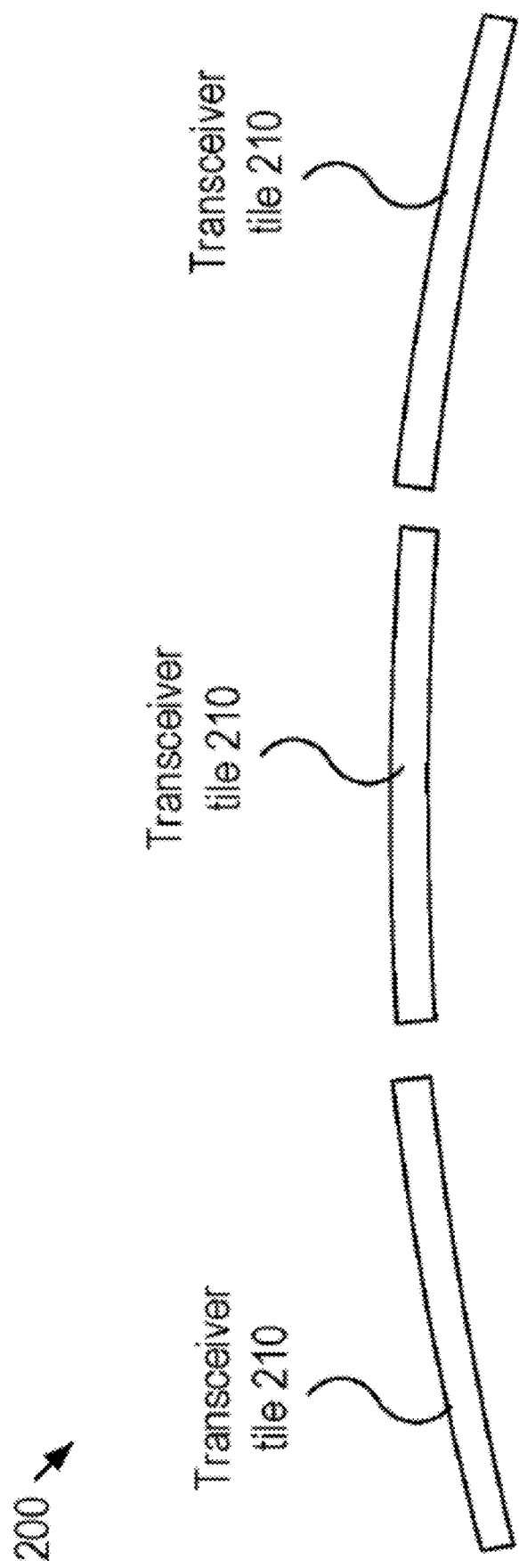
FIG. 3A shows a side view of a transceiver array according to embodiments of the present disclosure.
Figure 3B:
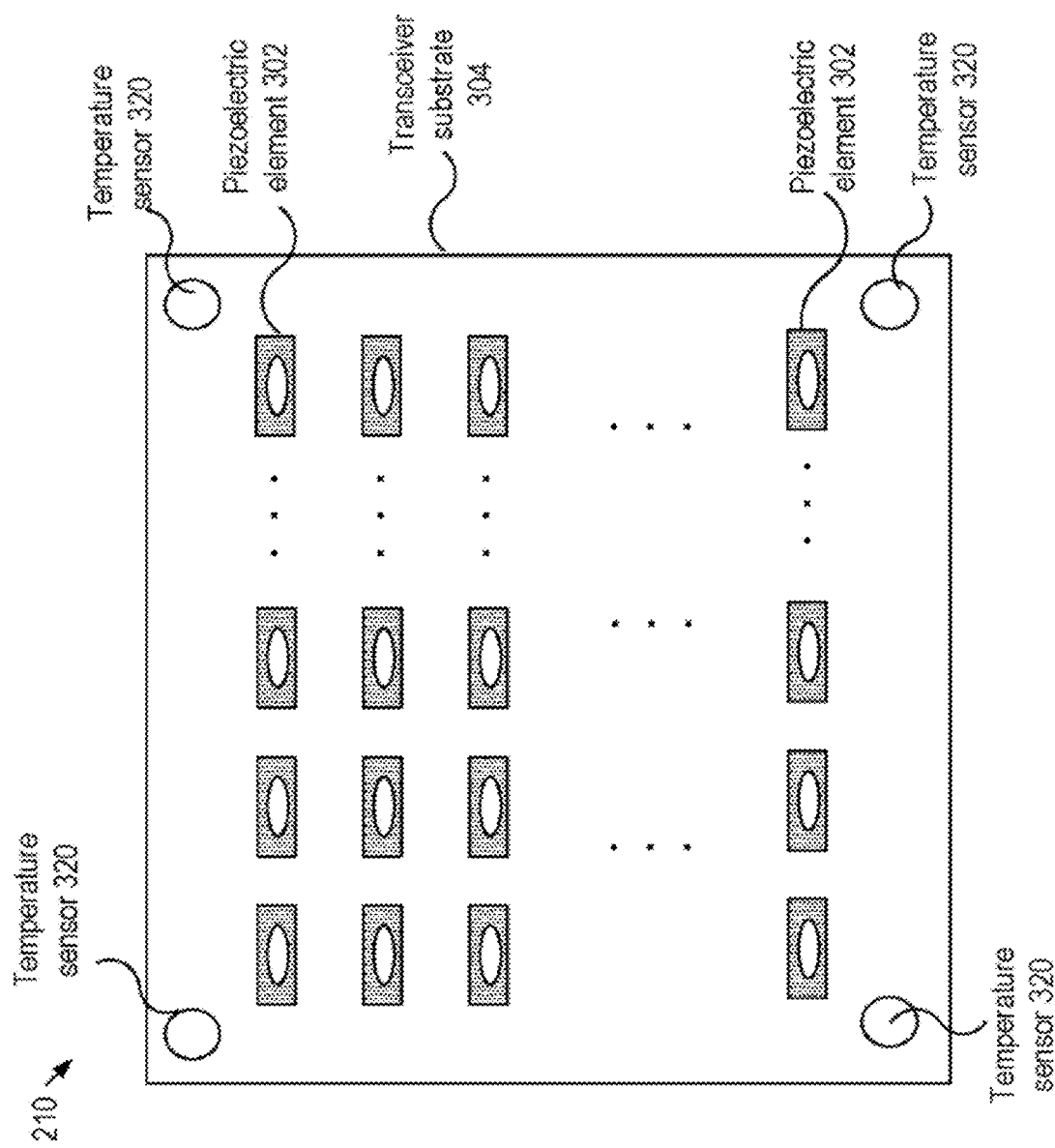
FIG. 3B shows a top view of a transceiver tile according to embodiments of the present disclosure.

FIG. 3A shows a side view of a transceiver array 200 according to embodiments of the present disclosure. FIG. 3B shows a top view of a transceiver tile 210 according to embodiments of the present disclosure. In embodiments, the array 200 may include one or more transceiver tiles 210. As depicted, the transceiver array 200 may include one or more transceiver tiles 210 arranged in a predetermined manner. For instance, as depicted in FIG. 3A, the transceiver tiles (or, shortly tiles) 210 may be physically bent to further form a curved transceiver array and disposed in the imager 120. It should be apparent to those of ordinary skill in the art that the imager 120 may include any suitable number of tiles and the tiles may be arranged in any suitable manner, and each tile 210 may include any suitable number of piezoelectric elements 302 having a concave or convex shape as described in greater detail herein, that are disposed on a transceiver substrate 304. On the substrate 304, one or multiple number of temperature sensors 320 may be placed in order to monitor the temperature of the transceiver tile 210 during operation. In embodiments, the transceiver array 200 may be a micro-machined array fabricated from a substrate.

Figure 4A:
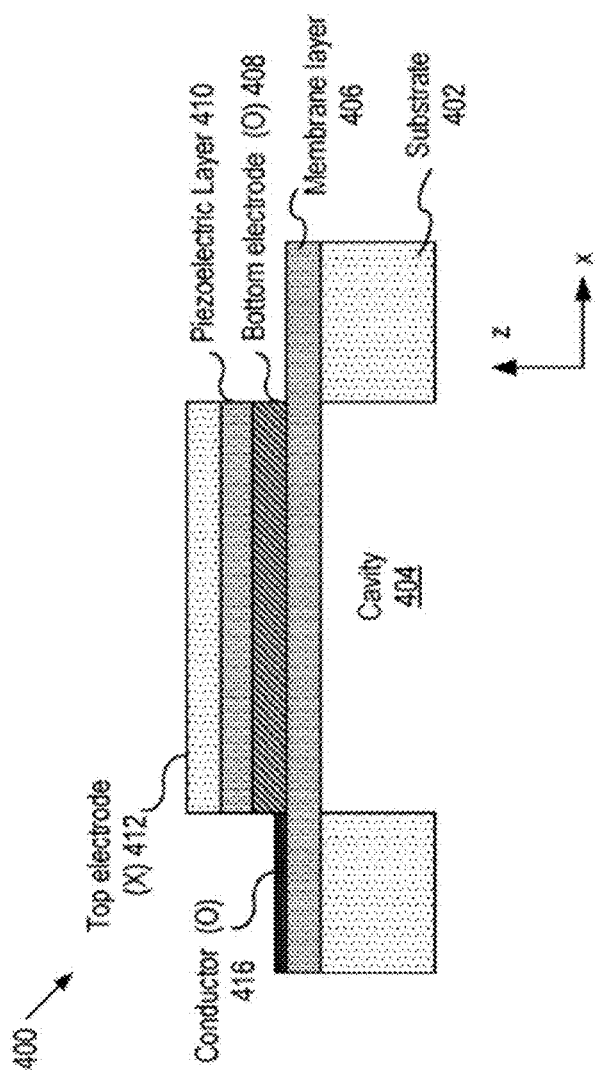
FIG. 4A shows a cross sectional view of a MUT, applicable to a concave or a convex MUT, taken along a direction 4-4 in FIG. 4B and FIG. 4D, according to embodiments of the present disclosure.

FIG. 4A shows a cross sectional view of a MUT 400, according to embodiments of the present disclosure. The cross sectional view of FIG. 4A is applicable to a concave or a convex MUT, according to embodiments of the present disclosure. As depicted, the concave or convex MUT may include: a membrane layer 406 suspended from a substrate 402; a first (e.g., bottom) electrode (O) 408 disposed on the membrane layer (or, shortly membrane) 406; a piezoelectric layer 410 disposed on the bottom electrode (0) 408; and a second (e.g., top) electrode (X) 412 disposed on the piezoelectric layer 410.

In embodiments, the substrate 402 and the membrane 406 may be one monolithic body and the cavity 404 may be formed to define the membrane 406. In embodiments, the cavity 404 may be filled with a gas at a predetermined pressure or an acoustic damping material to control the vibration of the membrane 406. In embodiments, the geometrical shape of the projection area of the top electrode 412 may be configured in a generally concave or convex shape having characteristic geometric parameters to control the dynamic performance and capacitance magnitude of the MUT 400.

In embodiments, each MUT 400 may by a pMUT and include a piezoelectric layer formed of at least one of PZT, KNN, PZT-N, PMN-Pt, AlN, Sc-AlN, ZnO, PVDF, and LiNiO3. In alternative embodiments, each MUT 400 may be a cMUT.

In embodiments, each MUT 400 may include additional electrodes and/or PZE layers. For example, as shown in FIG. 4F, the MUT 400 (be it concave, convex, or otherwise shaped as desired) may include: a membrane layer 406 suspended from a substrate 402; a first electrode (0) 408 disposed on the membrane layer (or, shortly membrane) 406; a first piezoelectric layer 410 disposed on the first electrode (0) 408; a second electrode 414 disposed on the first piezoelectric layer 410; a second piezoelectric layer 410 disposed on the second electrode 414; and a third electrode (X) 412 disposed on the second piezoelectric layer 410. Additional piezoelectric layers 410 and electrodes may be added as desired. In at least some instances, adding additional piezoelectric layers and/or electrodes (i.e., "sandwiching" electrodes and piezoelectric layers) increases the amplitude/dB output of the MUT 400.

In FIGS. 4B-4E, each MUT 400 is shown to have either a concave or convex shape. In embodiments, each concave MUT may include a top electrode that has a concave shape when viewed from the top of the MUT 400. In embodiments, each convex MUT may include a top electrode that has a convex shape when viewed from the top of the MUT 400. Hereinafter, the term shape of the top electrode 412 refers to a two-dimensional shape of the top electrode obtained by projecting the top electrode on to the x-y plane. Also, the shape of the top electrode is called symmetric if the shape is symmetric with respect to the two lines 450 and 452, where the lines 450 and 452 are parallel to the x- and y-axes, respectively, and pass through the midpoint of the top electrode on the x-axis. Also, hereinafter, the x-axis, also referred to herein as the major axis, extends along the direction where the top electrode has the longest dimension. The y-axis, also referred to herein as the minor axis, extends along the direction normal to the x- or major axis in the x-y plane, along the direction where the top electrode has the shortest dimension.

Figure 4B:
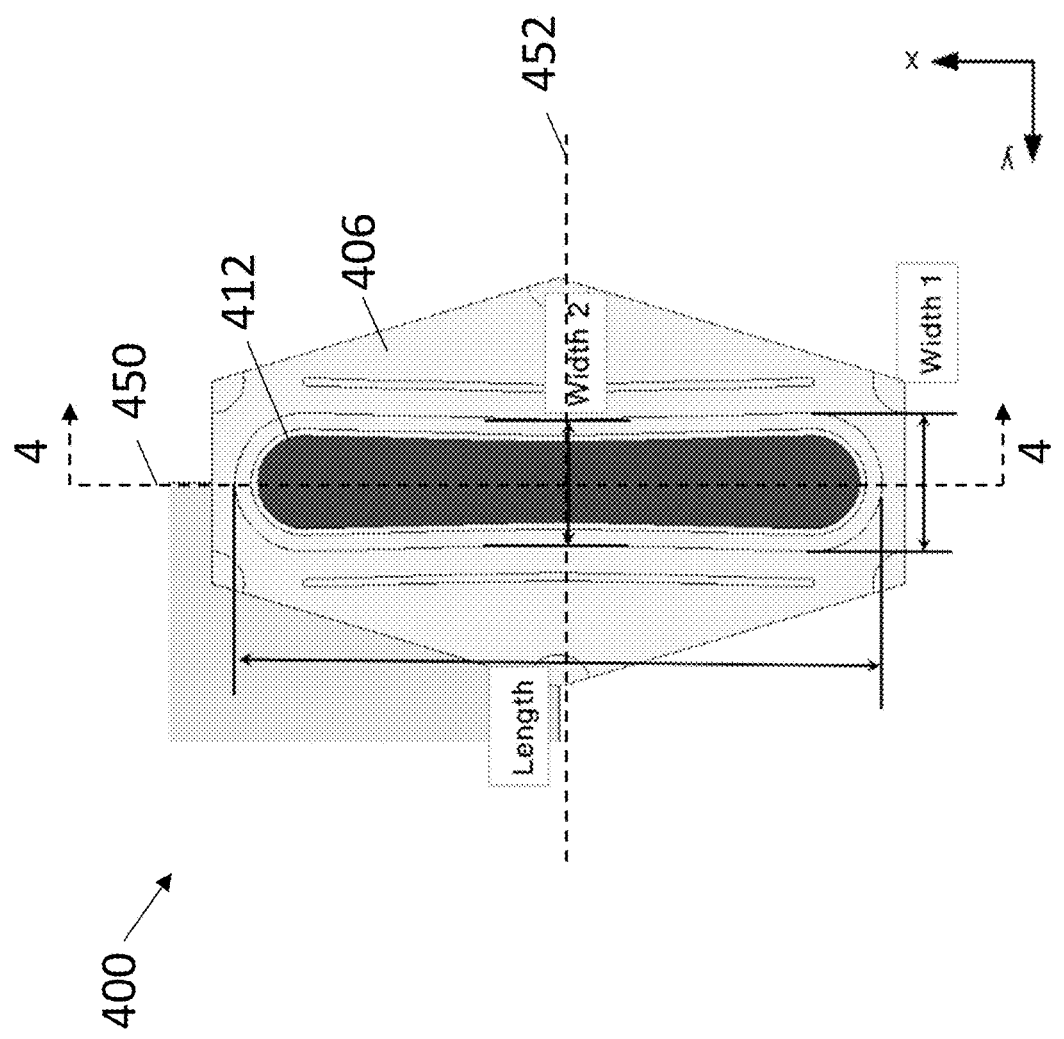
FIG. 4B shows a top view of a concave MUT according to embodiments of the present disclosure.
Figure 4C:
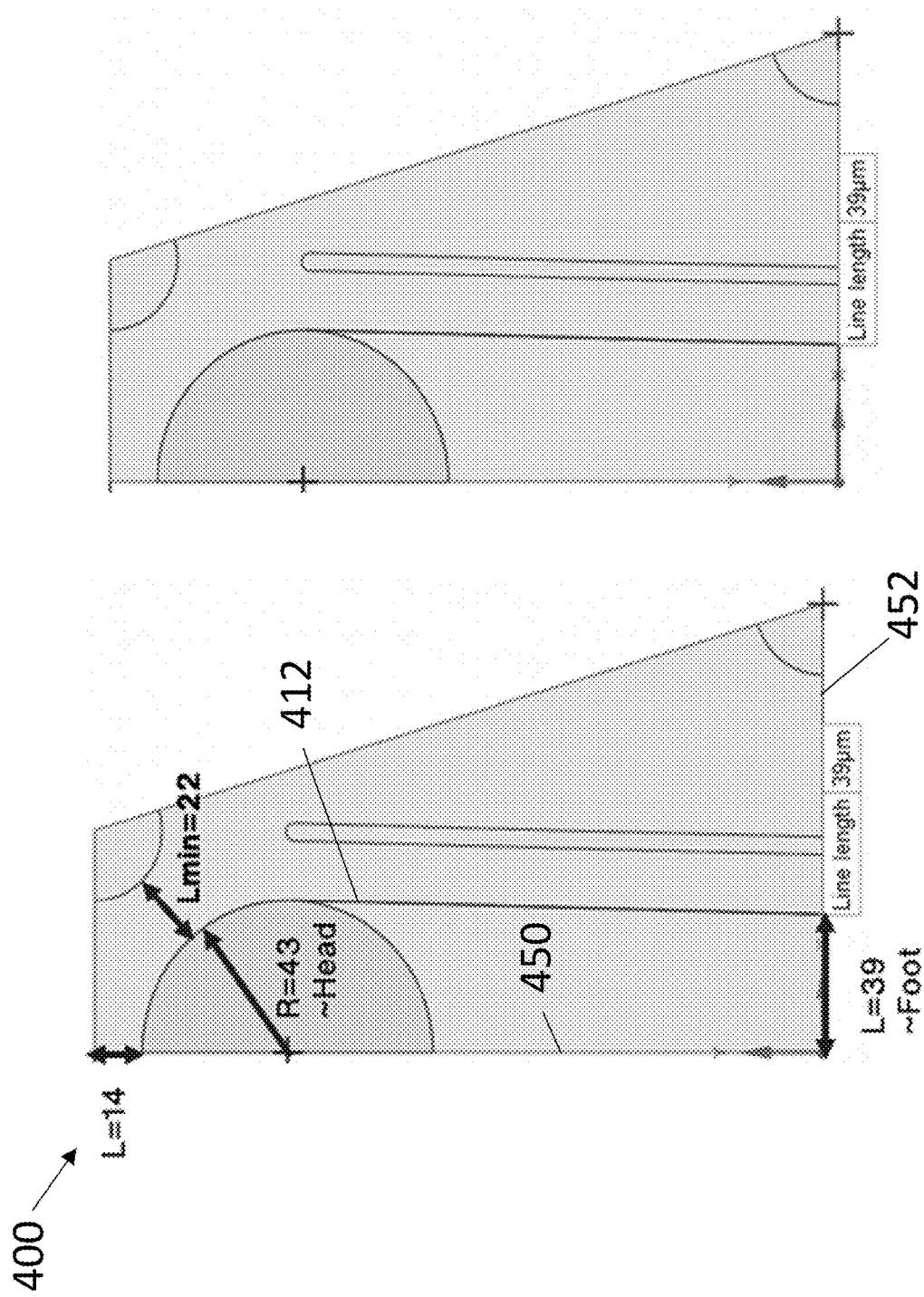
FIG. 4C shows an alternative top view of a concave MUT according to embodiments of the present disclosure.
Figure 4F:
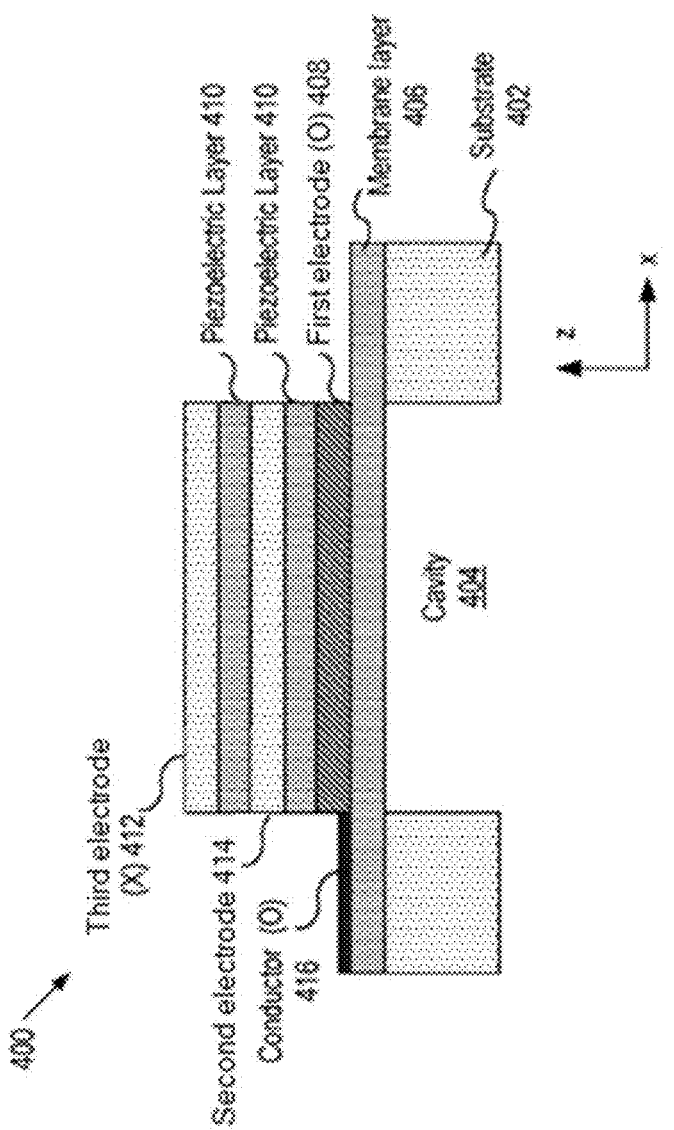
FIG. 4F shows a cross sectional view of another MUT, applicable to a concave or a convex MUT, taken along a direction 4-4 in FIG. 4B and FIG. 4D, according to embodiments of the present disclosure.

Whether the concave MUT of FIGS. 4B-4C or the convex MUT of FIGS. 4D-4E, the shape of the top electrode is defined by a major and minor axis, where the major and minor axis intersect at an origin point. Both distal ends of the top electrode, i.e., the ends of the top electrode farthest from the origin in the direction of the major axis, also referred to herein as the "heads" of the electrode, are defined by a radius of curvature, R. The characteristic half-width of the top electrode, also referred to herein as the "foot" of the electrode, is defined by a length L measured from the origin, in the direction of the minor axis (i.e., normal to the major axis), to the electrode outer edge or perimeter. The total width of the electrode at either its narrowest point (if a concave MUT) or its widest point (if a convex MUT) is two times L (i.e., 2 L). Edges of the electrode between the head and foot of the electrode may be curved or straight.

Alternatively, the heads of the electrodes may be straight or be defined by other curvature geometries that are not entirely circular. In at least some instances, it may be beneficial to avoid head or other) geometries that create localized areas of concentrated mechanical stress, which may enable a local mechanical or material failure mode, such as might be created if the head (or foot, for example) were defined by two straight lines converging at a sharp point.

In some embodiments, the head need not be circular, but may also be defined by, without limitation, non-circular curvature such as that of a parabola. Whereas a circular electrode head might be defined by a radius of curvature, R, the relevant parameter for a parabolic-shaped head might be the semilatus rectum of the parabola, defined as twice the distance between the parabola focus and vertex. Furthermore, the perimeter between the head and the foot may be defined either by a straight line or curvature and still be within the scope of this invention.

As illustrated in FIGS. 4B-4C, when the ratio of the radius of curvature over the characteristic width, R/L, is more than one, the top electrode is wider at its ends, or heads, as compared to its width at the middle, or foot, and the electrode has a generally concave geometry. As one of ordinary skill in the art would appreciate, variations of this concave MUT geometry are possible and still within the scope of this disclosure by varying the R/L, ratio, so long as R/L, is more than one, i.e., R>L. For example, for a top electrode having a head radius of curvature, R, of 43 micrometers, suitable foot width, L, of between approximately 37 and 41 micrometers would fall within the scope of this disclosure and exhibit the enhanced pressure amplitude and frequency response behavior when driven at fundamental and harmonic frequencies, as will be further described herein. On the other hand, if R/L is too large, whereby the head radius or curvature R is much larger than the foot width, L, the top electrode may not exhibit the desired pressure amplitude and frequency response behavior when driven at fundamental and harmonic frequencies, and can even experience structural failure.

As illustrated in FIGS. 4D-4E, when the ratio of the radius of curvature over the characteristic width, R/L, is less than one, the top electrode is narrower at its ends as compared to its width at the middle, and the electrode has a generally convex geometry. As one of ordinary skill in the art would appreciate, variations of this convex MUT geometry are possible and still within the scope of this disclosure by varying the R/L ratio, so long as R/L is less than one, i.e., R<L. For example, for a top electrode having a head radius of curvature, R, of 43 micrometers, suitable foot width, L, of between approximately 43.1 and 500 micrometers would fall within the scope of this disclosure and exhibit the enhanced pressure amplitude and frequency response behavior when driven at fundamental and harmonic frequencies, as will be further described herein. On the other hand, if R/L is too small, whereby the head radius or curvature R is much smaller than the foot width, L, the top electrode suffers from undesirable pressure amplitude and frequency response behavior when driven at fundamental and harmonic frequencies, and can even experience structural failure.

Whether configured with either concave or convex geometry, electrodes with certain R/L, values or within certain R/L, value ranges exhibit desirable pressure amplitude and frequency response behavior when driven at fundamental and harmonic frequencies, relative to certain prior electrode shape designs. The areal density distribution of the concave or convex electrode along an axis has a plurality of local maxima, wherein locations of the plurality of local maxima coincide with locations where a plurality of anti-nodal points at a vibrational resonance frequency are located. In general, the acoustic pressure performance, which refers to the energy of an acoustic pressure wave generated by each MUT at a frequency, may increase as the peak amplitude of the MUT increases at the frequency.

The ratio or R/L, may be driven by the desired behavior of the MUT. Changing the R/L, parameter of the electrode (and therefore, the geometry of the electrode) varies the pressure amplitude and frequency response behavior of the electrode. R/L may be large or small without limitation, so long as the electrode exhibits the desired pressure amplitude and/or frequency response behavior. The design requirements of the particular transducer, which may be dictated by factors such as transducer end use case (e.g., industrial, medical diagnosis, etc.), power requirements, operating mode requirements, etc., inform whether the pressure amplitude and frequency response exhibited by a particular R/L geometry is acceptable or desirable. Additional considerations such as fabrication and material capabilities may further limit the desirable or available range acceptable R/L, ranges.

Figure 5A:
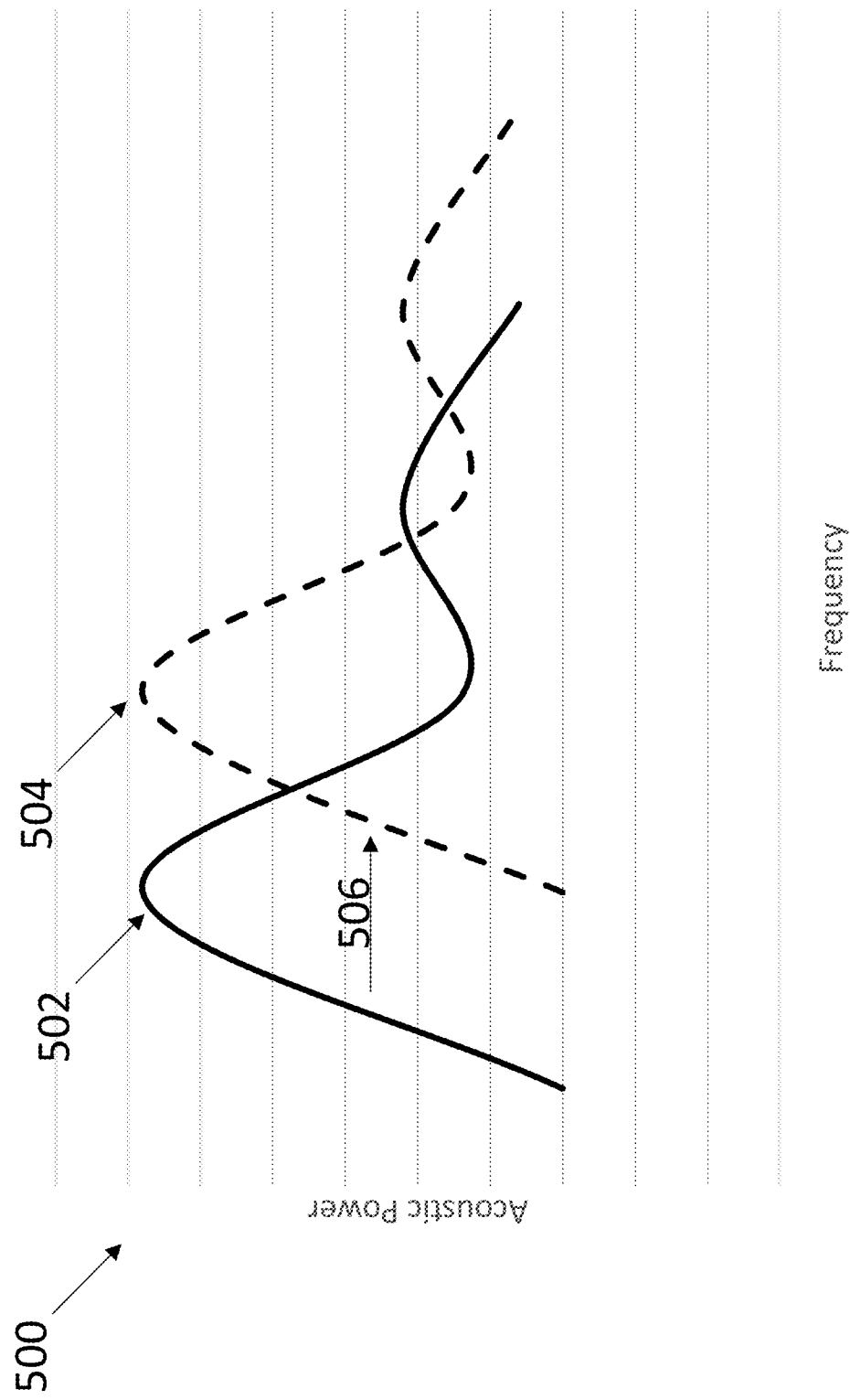
FIG. 5A shows a plot of acoustic responses of a MUT having a concave configuration according to embodiments of the present disclosure.
Figure 5B:
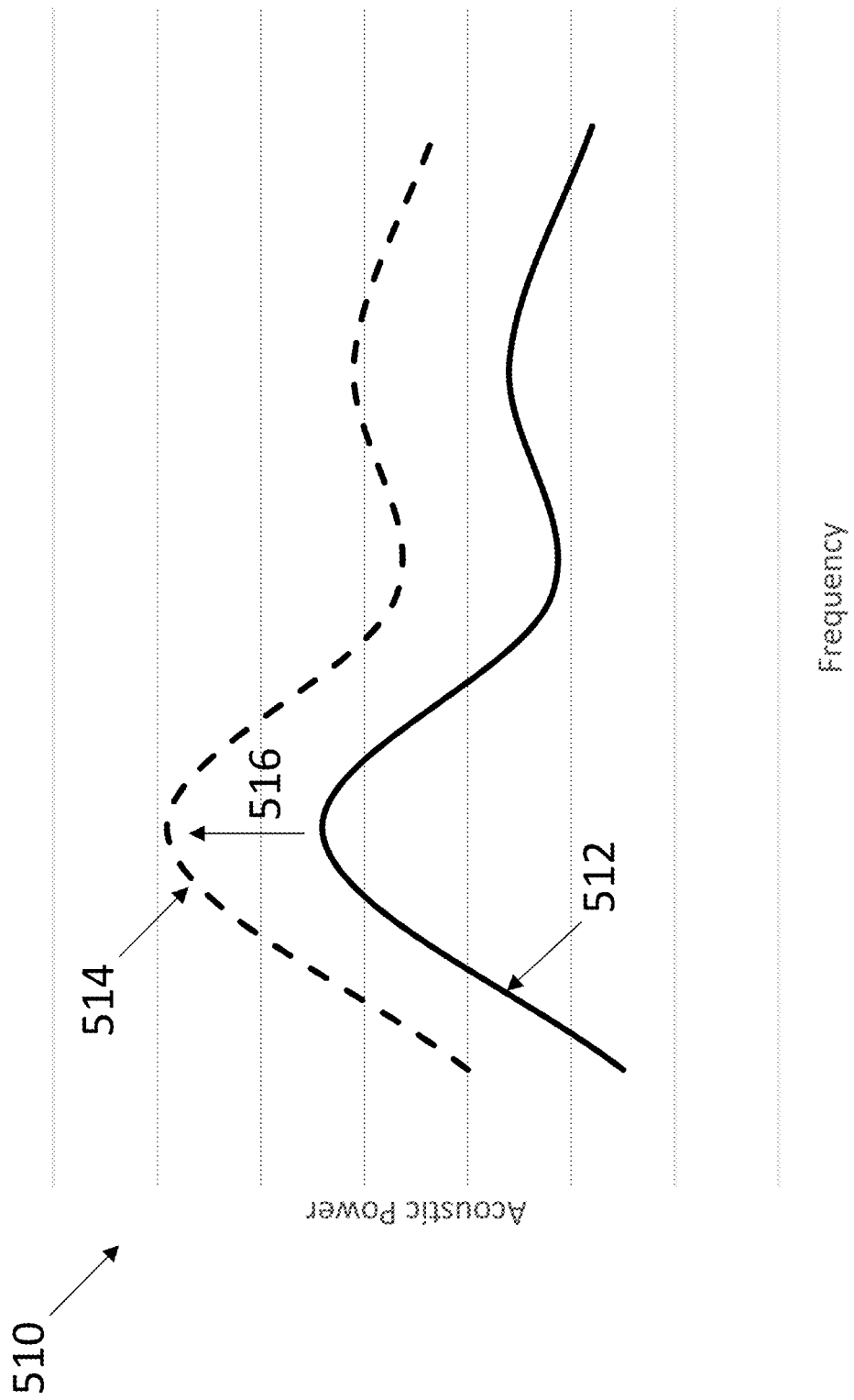
FIG. 5B shows a plot of acoustic responses of a MUT having a convex configuration according to embodiments of the present disclosure.

FIGS. 5A-5B show exemplary idealized plots 500 and 510 of acoustic responses of a MUT having a concave configuration and a MUT having a convex configuration, according to embodiments of the present disclosure. FIG. 5A shows an idealized plot 500 of how acoustic power changes with frequency for a concave MUT 504 (e.g., R/L>1) compared to a MUT 502 with R/L=1. FIG. 5B shows an idealized plot 510 of how acoustic power changes with frequency for a convex MUT 514 (e.g., R/L<1) compared to a MUT 512 with R/L=1. For concave MUT 504, as indicated by arrow 506, as R/L increases, the power-frequency curve shifts to the right compared to MUT 502. For convex MUT 514, as indicated by arrow 516, as R/L, decreases, the power-frequency curve shifts to the upwards compared to MUT 512.

Further modifications to the concave or convex MUT geometry, including varying the thickness of the membrane (e.g., a silicon membrane), or adding single or double notches at the periphery of the membrane (such that the membrane behaves more like a pinned beam or spring, rather than a cantilevered beam) may provide further enhanced performance characteristics. Examples of such modifications can be found in U.S. patent application Ser. Nos. 17/018,304 and 15/820,319, which are incorporated herein by reference.

Figure 6A:
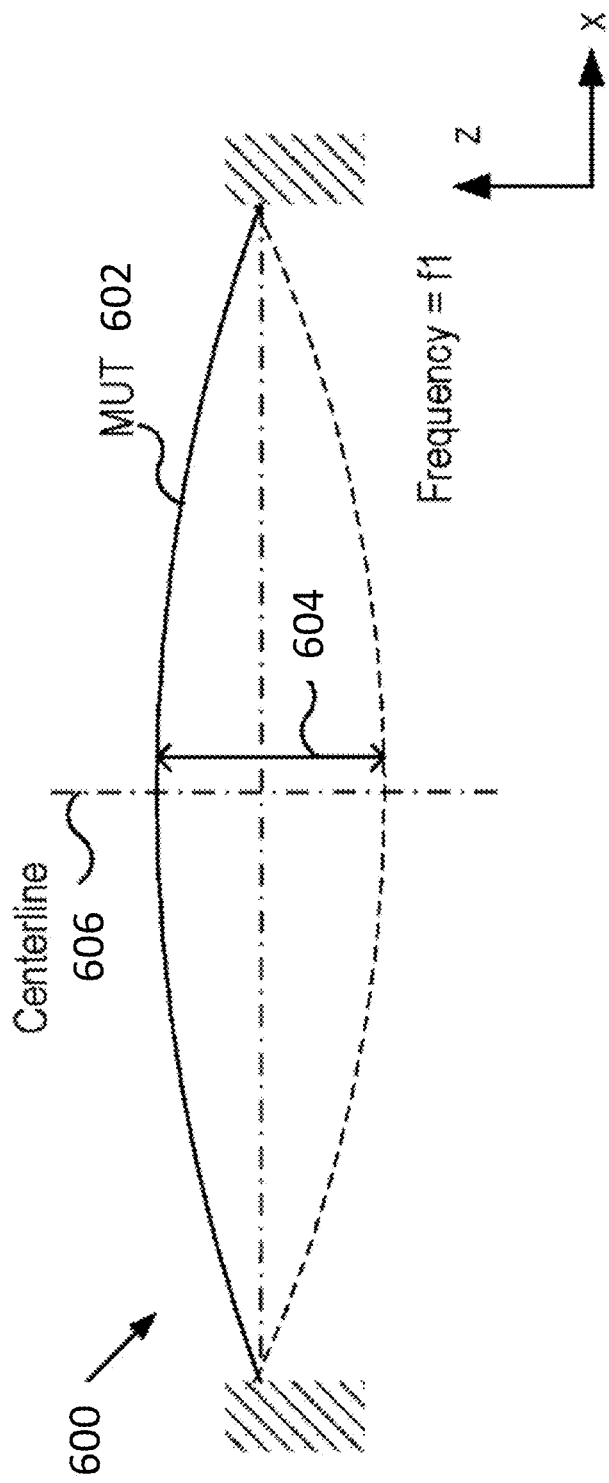
FIGS. 6A-6C show vibrational mode shapes of concave and convex MUTs according to embodiments of the present disclosure.
Figure 6B:
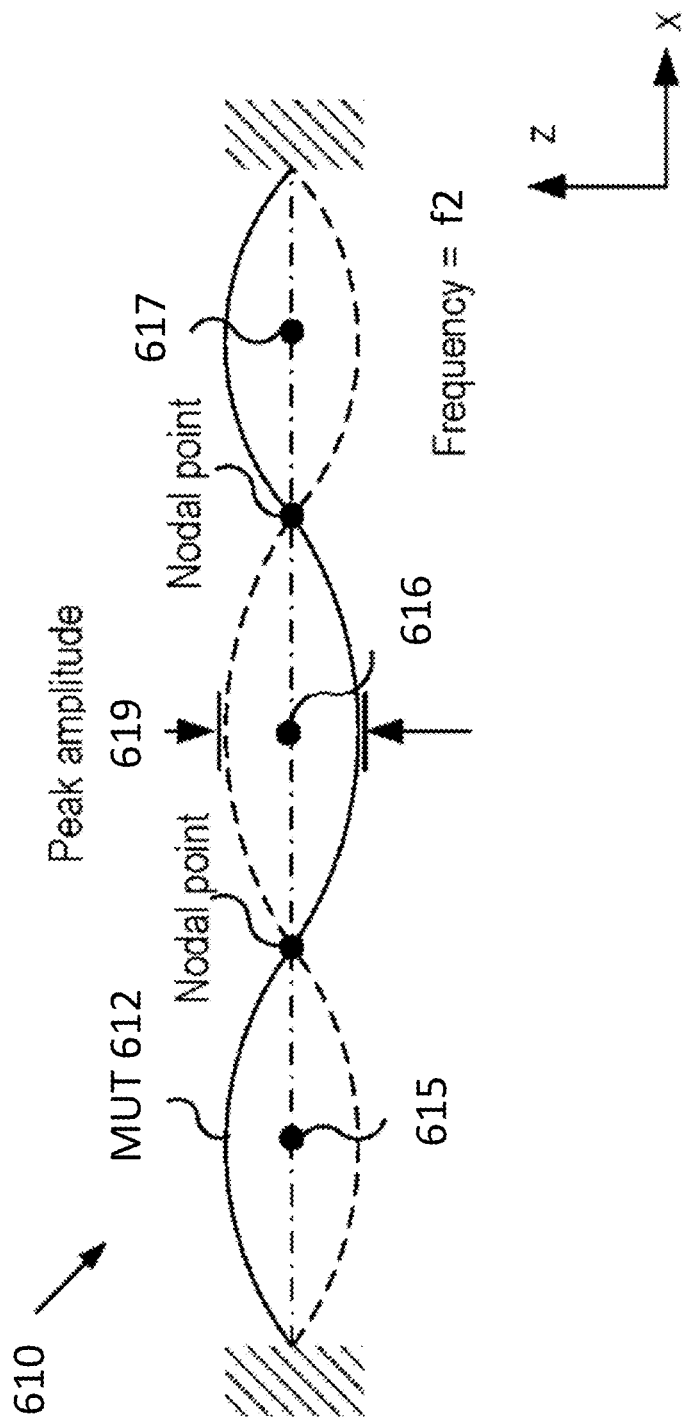
Figure 6C:
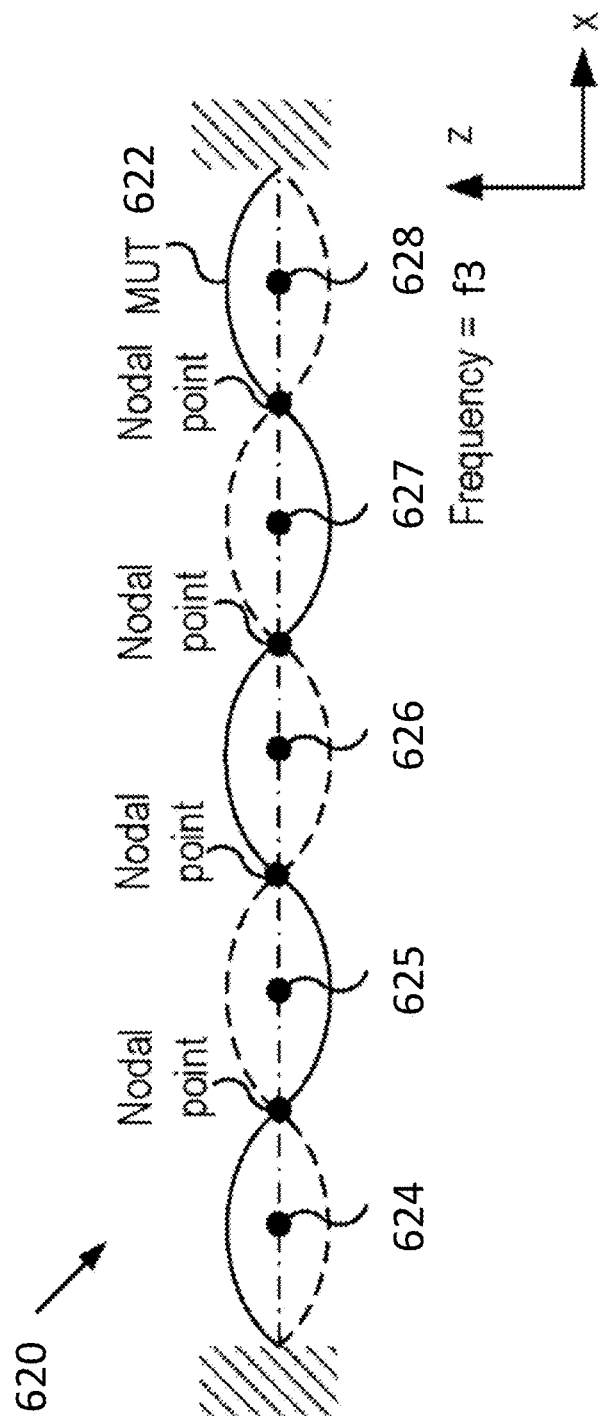

FIGS. 6A-6C show three vibrational modes 600, 610, 620, according to embodiments of the present disclosure. In FIGS. 6A-6C, each of the MUTs 602, 612, and 622, whether concave or convex, is represented by a single line for the purpose of illustration, where each single line shows the curvature of the stack of layers in a MUT. During operation, the stack of layers having the membrane 406, bottom electrode 408, piezoelectric layer 410, and top electrode 412 may move as a single body in the vertical direction, and may be deformed to have the curvature of the single line on the x-z plane. Also, the lines 602, 612, and 622, that correspond to different vibrational modes show the curvatures of the stack at different vibrational modes. In general, the resonance characteristics of a concave MUT and a convex MUT are similar to one another, though local gain may change depending on whether the MUT is concave or convex. In some instances, selection of a convex geometry or a concave geometry may be driven the gain improvements achieved at certain frequencies of interest.

In embodiments, the three vibrational modes 600, 610, and 620 may be associated with three vibrational resonance frequencies, f1, f2, and f3, respectively. In FIGS. 6A-6C, only three vibrational modes are shown. However, it should be apparent to those of ordinary skill in the art that a concave or convex MUT may operate in more than three vibrational resonance modes (or shortly vibrational modes).

In FIG. 6A, the concave or convex MUT 602 may operate in the first vibrational mode 600, where the arrow 604 indicates that the MUT 602 (more specifically, the stack of layers) moves in the vertical direction in the first mode 600. In embodiments, the first vibrational mode 600 may be symmetric, i.e., the mode shape is symmetric with respect to the centerline 606 of the MUT. In embodiments, the shape of the top electrode of the MUT 602 may be symmetric and either be concave or convex, as shown in FIGS. 4B-4E.

In FIG. 6B, the MUT 612 may operate in the second vibrational mode 610. In embodiments, the second vibrational mode 610 may be symmetric, i.e., the mode shape is symmetric with respect to the centerline 606. Hereinafter, the term symmetric vibrational mode refers to a vibrational mode where the locations of the anti-nodal points, such as 615, 616, and 617, (i.e., the peak amplitudes) are arranged symmetrically with respect to a centerline 606, and the centerline 606 represents a line that is parallel to the z-axis and passes through the midpoint of the MUT on the x-axis.

In the second vibrational mode 610, the MUT 612 may have two nodal points and three anti-nodal points (or equivalently, three peak amplitude points) 615, 616, and 617. In embodiments, the shape of the top electrode of the MUT 612 may be symmetric and either be concave or convex, as shown in FIGS. 4B-4E.

In FIG. 6C, the MUT 622 may operate in the third vibrational mode 620. In embodiments, the third vibrational mode 620 may be symmetric, i.e., the mode shape is symmetric with respect to the centerline 606. In the third vibrational mode, the MUT 622 may have four nodal points and five anti-nodal points (i.e. five peak amplitude points) 624, 625, 626, 627, and 628. In embodiments, the shape of the top electrode of the MUT 622 may be symmetric and either be concave or convex, as shown in FIGS. 4B-4E.

In general, the acoustic pressure performance, which refers to the energy of an acoustic pressure wave generated by each MUT at a frequency, may increase as the peak amplitude of the MUT increases at the frequency. However, relative to a convex MUT of same or similar total area, the concave MUT has greater local area distributions at the distal ends compared to the middle (i.e., R>L). As a consequence, relative to a convex MUT of same or similar area, the concave MUT is able to output higher acoustic pressure amplitude, particularly at harmonic frequencies.

It is noted that each of the MUTs 302 in FIG. 3 may be a piezoelectric micromachined ultrasound transducer (pMUT). However, it should be apparent to those of ordinary skill in the art that the transceiver tile 210 may include an array of capacitive micromachined ultrasound transducers (cMUTs), i.e., the piezoelectric elements 302 may be replaced by cMUTs. In such a case, the top electrode of a CMUT may have a shape that is similar to one of shapes of the top electrodes 412, so that the acoustic response of the cMUT is controlled at various vibrational resonance frequencies, based on the principles described in conjunction with FIGS. 4B-6C.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A micromachined ultrasonic transducer (MUT), comprising:
a first electrode, when seen in a top view, having first and second end portions along a first axis that extends in a longitudinal direction of the first electrode, the first end portion and the second end portion comprising semicircular shapes each having a constant radius of curvature R,
wherein a second axis extends in a transverse direction perpendicular to the first axis and passes through a midpoint of the first electrode, the midpoint having a longitudinal location along the first axis, the first electrode being symmetric about both the first axis and the second axis and defining an outer perimeter having longitudinal edges that bend around the midpoint such that the shape has a widest transverse width at the longitudinal location of the midpoint,
wherein a half-width of the first electrode is defined by a length L measured from the midpoint, along the second axis, to the outer perimeter of the first electrode,
wherein a total width of the first electrode at the widest transverse width is greater than 2R such that the longitudinal edges of the first electrode on either side of the first axis at the first electrode's widest point has a convex shape, and
wherein R/L is less than 1.

2. The MUT of claim 1, wherein the MUT is a capacitive micromachined ultrasound transducer (cMUT).

3. The MUT of claim 1, wherein the MUT is a piezoelectric micromachined ultrasound transducer (pMUT).

4. The MUT of claim 1, further comprising:
a substrate;
a membrane suspending from the substrate;
a second electrode disposed on the membrane; and
a piezoelectric layer disposed on one or more of the first electrode or the second electrode.

5. The MUT of claim 4, wherein the piezoelectric layer comprises a first piezoelectric layer disposed on the second electrode, and further comprising:
a third electrode disposed on the first piezoelectric layer; and
a second piezoelectric layer disposed on the third electrode,
wherein the first electrode is disposed on the second piezoelectric layer.

6. The MUT of claim 4, wherein the piezoelectric layer is formed of at least one of PZT, KNN, PZT-N, PMN-Pt, AlN, Sc-AlN, ZnO, PVDF, and LiNiO3.

7. An imaging device, comprising:
a transducer array including a plurality of micromachined ultrasonic transducers (MUTs), each of the plurality of MUTs comprising:
an electrode having opposing first and second heads, a longitudinal axis extending from the first head to the second head, a transverse axis that passes through the longitudinal axis at a widest point of the electrode, and a perimeter that, when viewed from a top view, is (i) symmetric about the longitudinal and transverse axes and (ii) has a convex midsection formed by two longitudinal edges extending between the first and second heads, each longitudinal edge having two straight sections that are oriented transverse relative to each other and converge at the transverse axis of the electrode.

8. The imaging device of claim 7, wherein the MUTs are capacitive micromachined ultrasound transducers (cMUTs).

9. The imaging device of claim 7, wherein the MUTs are piezoelectric micromachined ultrasound transducers (pMUTs).

10. The imaging device of claim 7, wherein the transverse axis passes through the longitudinal axis at a midpoint of the electrode.

11. The imaging device of claim 7, wherein each MUT comprises:
a substrate;
a membrane suspending from the substrate;
a second electrode disposed on the membrane; and
a piezoelectric layer disposed on one or more of the first electrode or the second electrode.

12. The imaging device of claim 11, wherein the piezoelectric layer comprises a first piezoelectric layer disposed on the second electrode, and further comprising:
a third electrode disposed on the first piezoelectric layer; and
a second piezoelectric layer disposed on the third electrode,
wherein the first electrode is disposed on the second piezoelectric layer.

13. The MUT of claim 1, wherein a desired pressure amplitude and frequency response occurs when the MUT is driven at fundamental and harmonic frequencies.

14. The MUT of claim 1, wherein acoustic pressure performance increases as a peak amplitude of the MUT increases.

15. The MUT of claim 1, wherein the longitudinal edges comprise straight sections that converge at the second axis.

16. The MUT of claim 15, wherein each longitudinal edge comprises a first straight portion and a second straight portion oriented such that a line extending from the first straight portion would meet a line extending from the second straight portion in an obtuse angle.

17. A micromachined ultrasonic transducer comprising an elongate electrode body having a longitudinal axis, a width measured normal to the longitudinal axis, and an extended waist portion at which the width extends to a maximum width along the longitudinal axis at a midpoint of the electrode body, the electrode body being symmetric about the waist portion and about the longitudinal axis such that the electrode body has two sides opposite the longitudinal axis that each comprise straight portions that bend around the midpoint.

18. The transducer of claim 17, wherein the electrode body defines first and second semi-circular end portions, the end portions being defined by a constant radius of curvature R.

19. The transducer of claim 18, wherein the width of the waist portion is greater than 2R.

20. The transducer of claim 17, wherein the two sides each have comprise straight portions that converge at the waist portion on each side.

21. The transducer of claim 17, wherein the transducer is a piezoelectric micromachined transducer (pMUT).

* * * * *